United States Patent
Kuramochi

(10) Patent No.: US 10,228,362 B2
(45) Date of Patent: Mar. 12, 2019

(54) MEASUREMENT APPARATUS

(71) Applicant: ADVANTEST CORPORATION, Nerima-ku, Tokyo (JP)

(72) Inventor: Yasuhide Kuramochi, Tokyo (JP)

(73) Assignee: ADVANTEST CORPORATION, Tokyo (JP)

( * ) Notice: Subject to any disclaimer, the term of this patent is extended or adjusted under 35 U.S.C. 154(b) by 562 days.

(21) Appl. No.: 14/925,022

(22) Filed: Oct. 28, 2015

(65) Prior Publication Data

US 2016/0153961 A1    Jun. 2, 2016

(30) Foreign Application Priority Data

Nov. 28, 2014  (JP) .................................. 2014-242022

(51) Int. Cl.
  *G01N 33/487*    (2006.01)
  *C12Q 1/6869*    (2018.01)

(52) U.S. Cl.
  CPC ..... *G01N 33/48721* (2013.01); *C12Q 1/6869* (2013.01)

(58) Field of Classification Search
  CPC .................. G01N 33/48721; C12Q 1/6869
  See application file for complete search history.

(56) References Cited

U.S. PATENT DOCUMENTS

| | | |
|---|---|---|
| 4,807,147 A | 2/1989 | Halbert et al. |
| 2010/0072080 A1 | 3/2010 | Karhanek et al. |
| 2010/0099198 A1 | 4/2010 | Zhao et al. |
| 2016/0153961 A1 | 6/2016 | Kuramochi |

FOREIGN PATENT DOCUMENTS

| | | |
|---|---|---|
| JP | H04198702 A | 7/1992 |
| JP | H06300513 A | 10/1994 |
| JP | H11101807 A | 4/1999 |

(Continued)

OTHER PUBLICATIONS

"Axon Axopatch 200B Microelectrode Amplifier," Modular Devices, 2012.

(Continued)

*Primary Examiner* — J. Christopher Ball
(74) *Attorney, Agent, or Firm* — Cantor Colburn LLP

(57) ABSTRACT

A measurement apparatus is provided that measures a current signal $I_{DUT}$ that flows through a device under test. A transimpedance amplifier converts the current signal $I_{DUT}$ into a voltage signal $V_{OUT}$. A digitizer converts the voltage signal $V_{OUT}$ into first digital data. A digital signal processing unit performs signal processing on the first digital data, and controls the measurement apparatus. The measurement apparatus has a configuration comprising two separate modules, i.e., a probe module which is located in the vicinity of the device under test during a measurement, and a backend module connected to the probe module via at least one cable. The transimpedance amplifier is built into the probe module.

18 Claims, 5 Drawing Sheets

(56) References Cited

FOREIGN PATENT DOCUMENTS

| | | | |
|---|---|---|---|
| JP | 2003240747 A | | 8/2003 |
| JP | 2006214792 A | | 8/2006 |
| JP | 2008107216 A | | 5/2008 |
| JP | 2010243494 A | | 10/2010 |
| JP | 2013019853 A | * | 1/2013 |
| JP | 2013019853 A | | 1/2013 |
| JP | 2013257334 A | | 12/2013 |
| WO | 2009157187 A1 | | 12/2009 |

OTHER PUBLICATIONS

"Axopatch 200B," Axon Instruments, 1998.
"Bringing patch-clamp noise down to unprecendented leves," Automate Science, 2015.
"The Axon Guide—2500-0102 Rev. C," Modular Devices, 2008.
USPTO Non-final Office Action corresponding to U.S. Appl. No. 14/925,047; dated Dec. 29, 2017.
U.S. Non-Final Office Action for corresponding to U.S. Appl. No. 14/925,047; dated Jun. 16, 2017.
Notification of Reason for Refusal for corresponding JP Application No. 2014-242023; dated Feb. 6, 2018.
Notification of Reasons for Refusal for corresponding JP Application No. 2014-242022; dated Feb. 6, 2018.
USPTO Final Office Action corresponding to U.S. Appl. No. 14/925,047; dated Jul. 30, 2018.
USPTO Non-Final Office Action corresponding to U.S. Appl. No. 14/925,047; dated Jan. 10, 2019.

* cited by examiner

MEASUREMENT APPARATUS

CROSS-REFERENCE TO RELATED APPLICATIONS

The present invention claims priority under 35 U.S.C. § 119 to Japanese Application No. 2014-242022, filed Nov. 28, 2014, the entire content of which is incorporated herein by reference.

BACKGROUND OF THE INVENTION

Field of the Invention
The present invention relates to a measurement apparatus.
Description of the Related Art
In order to analyze the base sequence of DNA (deoxyribonucleic acid), RNA (ribonucleic acid), or the like, a base sequence analyzing apparatus (sequencer) is employed. As a next-generation (fourth-generation) sequencer, various kinds of techniques have been sought by research institutions and industries. As one of such prospective techniques, the gating nanopore sequencing technique has attracted attention.

With the gating nanopore sequencing technique, DNA or RNA is moved such that it passes through a gap between a pair of nanometer-order electrodes (nano-electrodes). The tunnel current that flows through the electrode gap changes according to the base type (A, G, T, C) that passes through the electrode gap. The base sequence is determined based on the change in the tunnel current. This technique is anticipated to have the potential to provide a very low-cost and very compact-size apparatus that is capable of analyzing a base sequence. It should be noted that, in the present specification, examples of such a "nano-electrode" include sub-micro electrodes and micro electrodes having a larger size.

Also, as a method using a tunnel current in the same way as with the gating nanopore sequencing technique, the MCBJ (Mechanically Controllable Break Junction) method has been developed. With the MCBJ method, a nano-electrode is formed by breaking a metal wire.

As an important element technology, such a sequencer requires a current measurement device that is capable of measuring a tunnel current that flows through a nano-electrode gap with sufficiently high precision. That is to say, such a tunnel current has a current value on the order of several tens of picoampere (pA). Accordingly, in order to judge the base type, there is a need to detect a difference in conductance on the order of several picoseconds (ps).

SUMMARY OF THE INVENTION

The present invention has been made in view of such a situation. Accordingly, it is an exemplary purpose of an embodiment of the present invention to provide a measurement apparatus which is capable of reducing the effects of noise, thereby providing high-precision current measurement.

An embodiment of the present invention relates to a measurement apparatus that measures a current signal that flows through a device under test. The measurement apparatus comprises: a transimpedance amplifier that converts the current signal into a voltage signal; a digitizer that converts the voltage signal into first digital data; and a digital signal processing unit that performs signal processing on the first digital data, and that controls the measurement apparatus. The measurement apparatus has a configuration comprising a first module and a second module which are separated one another, and the first module is located in the vicinity of the device under test during a measurement, and the second module is coupled to the first module via at least one cable. The transimpedance amplifier is built into the first module.

By providing the first module with such a transimpedance amplifier as a built-in component, such an arrangement allows the current signal $I_{DUT}$ to be converted into the voltage signal $V_{OUT}$ at a position in the vicinity of the device under test, which functions as a signal generation source. This reduces the noise effects received by the transimpedance amplifier from the digital circuit, thereby providing high-precision measurement. Furthermore, by positioning the transimpedance amplifier in the vicinity of the device under test such that they are in contact with each other, such an arrangement reduces the input capacitance, thereby providing wide-bandwidth current measurement.

Also, the measurement apparatus according to an embodiment may further comprise: a guard metal member formed within the first module such that the guard metal member is located in the vicinity of a signal line via which the current signal $I_{DUT}$ is transmitted; and a guard amplifier that is built into the first module, and that applies a virtual ground voltage of the transimpedance amplifier to the guard metal member.

With such an embodiment, the guard metal members prevent noise from mixing in the signal line, thereby further reducing noise. Furthermore, by adjusting the electric potentials at the guard metal members by means of the guard amplifier, such an arrangement is capable of setting the guard metal members and the signal line to the same electric potential. Such an arrangement reduces the effects of a parasitic capacitance that occurs between these components, thereby providing wide-bandwidth current measurement.

Also, the measurement apparatus according to an embodiment may further comprise a first voltage source that is built into the first module, and that generates a first voltage that determines the virtual ground voltage of the transimpedance amplifier.

By generating the first voltage that determines the virtual ground voltage at a position in the vicinity of the transimpedance amplifier, such an arrangement is capable of preventing noise from being superimposed on the virtual ground voltage. This reduces the noise component included in the current signal $I_{DUT}$ or otherwise the voltage signal $V_{OUT}$.

Also, the first voltage source may generate the first voltage having a voltage level that corresponds to a first control signal generated by the digital signal processing unit.

In this case, such an arrangement is capable of adjusting the voltage level of the first voltage according to the measurement result obtained by the digital signal processing unit. Furthermore, such an arrangement is capable of supplying a suitable voltage to the device under test according to the state of the device under test. Furthermore, in a case in which the first voltage is feedback controlled, by performing the feedback control operation by means of the first module alone without involving the second module, such an arrangement provides a high-speed control operation. Also, in this case, the data is used in the feedback control operation without involving data transmission via a cable, thereby reducing noise emission.

Also, the measurement apparatus according to an embodiment may further comprise a second voltage source that is built into the first module, and that generates a second voltage to be supplied to the device under test.

By generating the second voltage, which is to be supplied to the device under test, at a position in the vicinity of the device under test, such an arrangement is capable of preventing noise from being superimposed on the second voltage. This reduces the noise component included in the current signal $I_{DUT}$ or otherwise the voltage signal $V_{OUT}$.

Also, the second voltage source may generate the second voltage having a voltage level that corresponds to a second control signal generated by the digital signal processing unit.

In this case, such an arrangement is capable of adjusting the voltage level of the second voltage according to the measurement result obtained by the digital signal processing unit. Furthermore, such an arrangement is capable of supplying a suitable voltage to the device under test according to the state of the device under test. Furthermore, in a case in which the second voltage is feedback controlled, by performing the feedback control operation by means of the first module alone without involving the second module, such an arrangement provides a high-speed control operation. Also, in this case, the data is used in the feedback control operation without involving data transmission via a cable, thereby reducing noise emission.

Also, the device under test may comprise a first electrode to be connected to the transimpedance amplifier and a second electrode that faces the first electrode. Also, a measurement target of the measurement apparatus may be a current that flows between the first electrode and the second electrode. Also, the virtual ground voltage of the transimpedance amplifier may be set to the ground voltage. Also, the second voltage source may supply the second voltage to the second terminal.

With such an embodiment, the second voltage is used as a bias voltage for the electrode pair. By generating the bias voltage at a position in the vicinity of the device under test, such an arrangement is capable of preventing noise from being superimposed on the bias voltage. This reduces the noise component included in the current signal $I_{DUT}$ or otherwise the voltage signal $V_{OUT}$.

Also, the first module may comprise a power supply terminal for receiving a DC power supply voltage.

With such an arrangement, there is no need to mount a switching power supply that functions as a noise source within the first module. Thus, such an arrangement is capable of preventing switching noise from mixing in the input of the transimpedance amplifier or other circuit nodes.

Also, the digitizer may be built into the first module.

By transmitting a measured signal converted in the form of digital data, such an arrangement provides improved resistance to noise in the data transmission process as compared with an arrangement employing analog transmission.

Also, the digital signal processing unit may comprise a first digital signal processing unit and a second digital signal processing unit. Also, the first digital signal processing unit may be built into the first module, may process the first digital data so as to generate a second digital data having a reduced amount of data, and may transmit the second digital data thus generated to the second module. Also, the second digital signal processing unit may be built into the second module, may receive the second digital data from the first digital signal processing unit, and may execute predetermined signal processing.

This reduces the amount of data transmitted from the first module to the second module. Such an arrangement is capable of providing a reduced data rate, thereby suppressing noise emission due to data transmission.

Also, the measurement apparatus may further comprise a waveform generator that is built into the first module, that receives digital waveform data, and that generates an analog voltage that corresponds to the digital waveform data thus received. Also, the digital signal processing unit may be built into the first module, and may include a third digital signal processing unit that generates the digital waveform data.

The analog voltage generated by the waveform generator may be used to drive the electrophoresis electrodes mounted on the device under test, or may be used to control the heater. By mounting both the third digital signal processing unit and the waveform generator on the first module, such an arrangement enables a high-speed control operation within the active probe module for controlling the voltage level, amplitude, and waveform of the analog voltage.

Also, the measurement apparatus may further comprise: an analog output terminal provided to the first module; and a first amplifier that is built into the first module, and that outputs, to an external circuit via the analog output terminal, a signal received from a predetermined internal node included within the first module.

For example, in a case in which the output of the transimpedance amplifier is used as such a predetermined node, a high-precision digitizer may be connected as an external circuit to the analog output terminal, and a microscopic current may be measured by means of the high-precision digitizer. Alternatively, the voltage at the analog output terminal may be used to calibrate the circuit included within the first module, or may be used to diagnose the device under test.

Also, the measurement apparatus may further comprise: an analog input terminal provided to the first module; a second amplifier that is built into the first module, and that supplies an analog signal input via the analog input terminal to the device under test as well as or otherwise a predetermined internal node included within the first module.

With such an embodiment, by connecting a high-precision waveform generator such as an arbitrary waveform generator, function generator, or the like to the analog input terminal, such an arrangement allows various kinds of control operations to be performed, examples of which include: controlling the heater or electrophoresis electrodes of the device under test, controlling the bias state of the device under test, and calibration of the internal circuit included within the first module.

Also, the measurement apparatus may further comprise: an oscillator that is built into the second module, and that generates a clock signal having a predetermined frequency; and a frequency multiplier that is built into the first module, and that multiplies the clock signal.

This allows the frequency of the clock signal to be transmitted from the second module to the first module to be reduced, thereby suppressing noise emission.

Also, the transimpedance amplifier may have a variable gain. Also, the digital signal processing unit may be built into the first module, and may comprise a gain controller that controls the gain according to the first digital data.

In this case, such an arrangement is capable of adjusting the gain according to the measurement result obtained by the digital signal processing unit. Furthermore, in a case in which the gain is feedback controlled, by performing the feedback control operation by means of the first module alone without involving the second module, such an arrangement provides a high-speed control operation. Also, in this case, the data is used in the feedback control operation without involving data transmission via a cable, thereby reducing noise emission.

Also, the measurement apparatus may further comprise a probe-through input terminal provided to the first module; and a probe-through output terminal provided to the first module, and that is connected to the probe-through input terminal.

With such an embodiment, by connecting an external apparatus to the probe-through input terminal, such an arrangement allows a special signal that depends on the device under test to be transmitted and received between the device under test and such an external apparatus. Thus, such an arrangement allows the measurement apparatus to measure various kinds of devices under test, thereby providing improved compatibility.

Also, the measurement apparatus may further comprise a data storage built into the second module.

Also, such an arrangement may suspend access to the data storage during the measurement of a microscopic current (during the sampling operation of the digitizer). Thus, such an arrangement is capable of further reducing noise that occurs in the current measurement.

Also, the measurement apparatus may further comprise a data storage detachably connected to the second module.

In this case, after the completion of a series of measurement steps by means of the measurement apparatus, such an arrangement allows a computer to analyze the data stored in the data storage. Also, with such an arrangement, such a computer does not access the data during the measurement operation of the measurement apparatus, thereby providing reduced noise.

Also, the measurement apparatus may further comprise a PC interface built into the second module. Also, the measurement apparatus may suspend the data transmission between itself and a PC during measurement of a microscopic current. This allows noise to be further reduced in the current measurement.

It is to be noted that any arbitrary combination or rearrangement of the above-described structural components and so forth is effective as and encompassed by the present embodiments.

Moreover, this summary of the invention does not necessarily describe all necessary features so that the invention may also be a sub-combination of these described features.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

The invention will now be described based on preferred embodiments which do not intend to limit the scope of the present invention but exemplify the invention. All of the features and the combinations thereof described in the embodiment are not necessarily essential to the invention.

In the present specification, the state represented by the phrase "the member A is connected to the member B" includes a state in which the member A is indirectly connected to the member B via another member that does not affect the electric connection therebetween, in addition to a state in which the member A is physically and directly connected to the member B.

Similarly, the state represented by the phrase "the member C is provided between the member A and the member B" includes a state in which the member A is indirectly connected to the member C, or the member B is indirectly connected to the member C via another member that does not affect the electric connection therebetween, in addition to a state in which the member A is directly connected to the member C, or the member B is directly connected to the member C.

[Basic Configuration]

Figure 1:
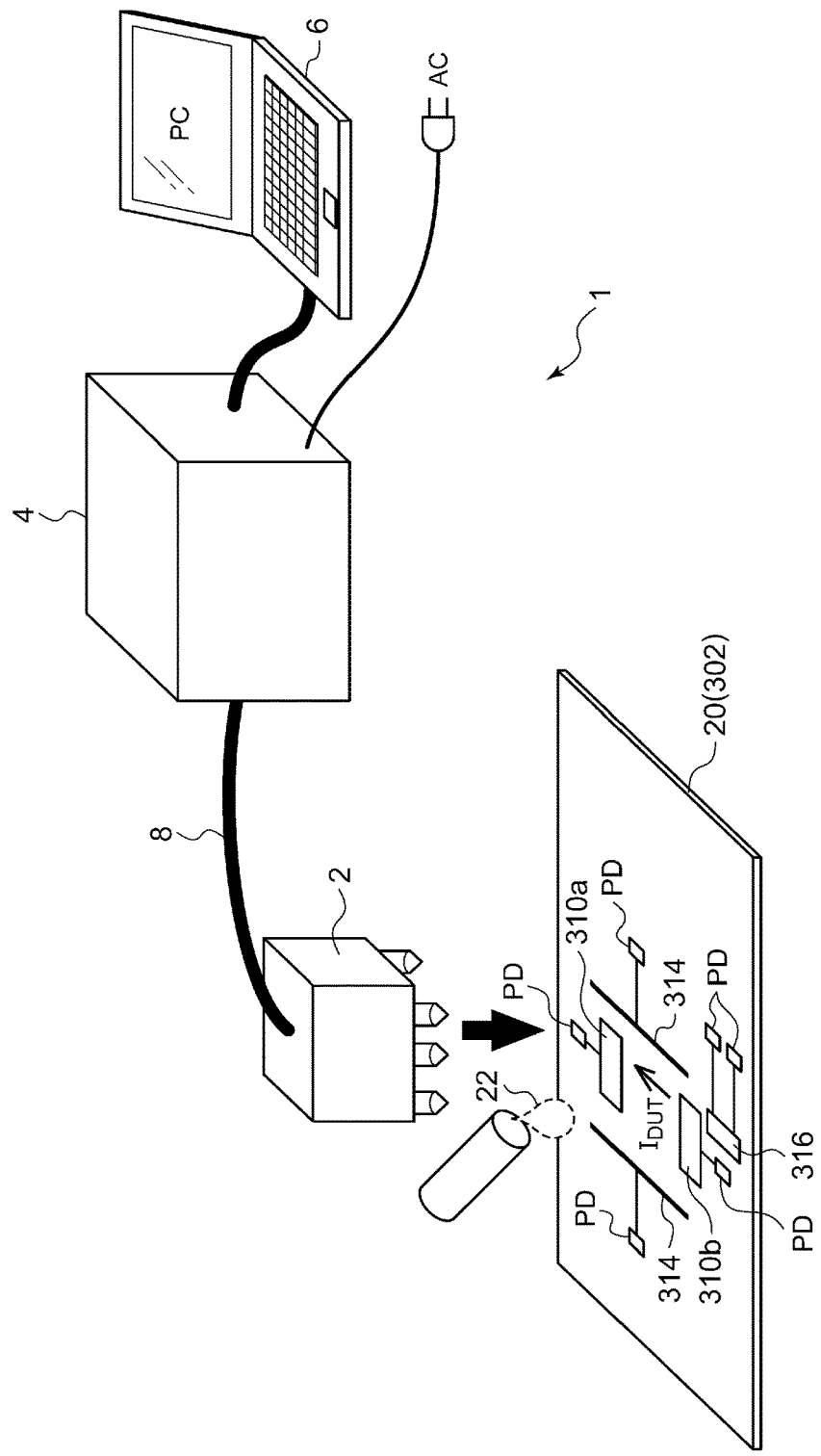
FIG. 1 is a block diagram showing a measurement apparatus according to an embodiment.

FIG. 1 is a block diagram showing a measurement apparatus 1 according to an embodiment. With the present embodiment, the measurement apparatus 1 is configured as a base sequence analyzing apparatus (sequencer).

For example, a device under test 20 is configured as a measurement chip (nanopore chip 302). The nanopore chip 302 includes an electrode pair 310, a pair of electrophoresis electrodes 314, a nanochannel, a nanopore structure, and the like formed on it. By controlling a DNA sample 22 such that it passes through the unshown nanochannel, such an arrangement is capable of separating and extracting such a DNA sample 22 in the form of a single molecule, thereby allowing the DNA sample 22 to be analyzed as a linear sample.

An analog voltage generated by the measurement apparatus 1 is applied to the electrophoresis electrodes 314. In this state, an electric field is generated between the electrophoresis electrodes 314 according to the analog voltage thus applied. Such an arrangement is capable of controlling the position of a DNA molecule.

The electrode pair 310 is formed within the nanopore structure (not shown). When a DNA molecule passes through the gap between the electrode pair 310, a tunnel current $I_{DUT}$ flows between the electrode pair 310 according to the DNA molecule base type that passes through the gap between the electrode pair 310. The measurement apparatus 1 identifies the base type based on the tunnel current (current signal) $I_{DUT}$.

A heater (heat source) 316 is arranged in the vicinity of the electrode pair 310 so as to control the temperature of the nanopore chip 302. A current is supplied to the heater 316 according to a signal received from the measurement apparatus 1, thereby generating Joule heat. The measurement apparatus 1 controls the amount of heat generation of the heater 316 so as to maintain the temperature at a position in the vicinity of the electrode pair 310 of the device under test 20 at a constant level.

Multiple pads PD are formed on the nanopore chip 302 so as to allow a signal to be supplied to each of the electrode pair 310, the electrophoresis electrodes 314, and the heater 316.

The measurement apparatus 1 measures the current signal $I_{DUT}$ that flows through the device under test 20.

The measurement apparatus 1 is mainly configured as two separate modules, i.e., an active probe module (first module, which will simply be referred to as the "probe module" hereafter) 2, and a digital backend module (second module, which will simply be referred to as the "backend module") 4. When the measurement is performed, the probe module 2 is set in the vicinity of the device under test 20. For example, probes or pins are provided to the probe module 2 such that they can be in contact with the pads PD formed on the device under test 20. The probe module 2 may be configured to be movable in the vertical direction. The backend module 4 is connected to the probe module 2 via at least one cable 8. The probe module 2 mainly mounts an analog frontend circuit. The backend module 4 mainly mounts a digital circuit.

Preferably, the probe module 2 and the backend module 4 are each covered by a metal housing so as to block external noise.

The measurement apparatus 1 measures the current signal $I_{DUT}$ that flows through the device under test 20, converts the current signal $I_{DUT}$ into a digital value, and identifies the base type based on the digital value thus converted. Furthermore, as described above, the measurement apparatus 1 supplies an appropriate voltage to the electrophoresis electrodes 314 and the electrode pair 310, and controls the heater 316.

The backend module 4 is connected to a computer 6. The computer 6 executes a program in order to control the probe module 2, the backend module 4, and other hardware components 10, 12, and 14.

Figure 2:
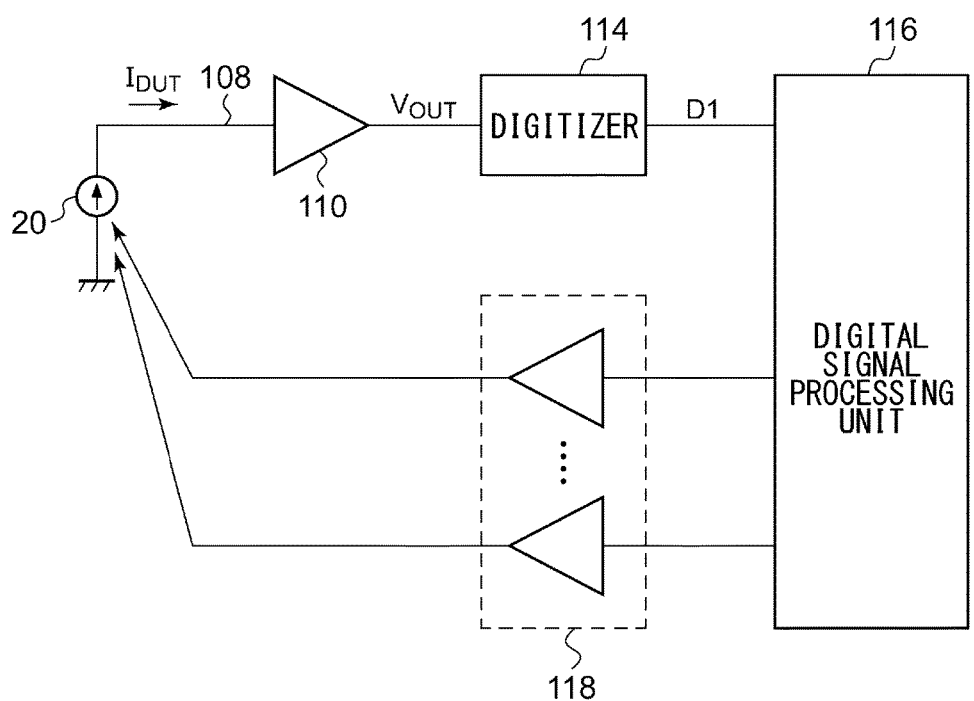
FIG. 2 is a function block diagram showing a measurement apparatus.

FIG. 2 is a function block diagram showing the measurement apparatus 1. The measurement apparatus 1 mainly includes a transimpedance amplifier 110, a digitizer 114, and a signal generating circuit 118.

The transimpedance amplifier 110 receives, via a signal line 108, the current signal $I_{DUT}$ generated by the device under test 20. Furthermore, the transimpedance amplifier 110 converts the current signal $I_{DUT}$ thus received into a voltage signal $V_{OUT}$. The digitizer 114 converts the voltage signal $V_{OUT}$ into first digital data D1. The digital signal processing unit 116 performs, based on the first digital data D1, a part of or otherwise all the steps of the digital signal processing necessary for identifying the base type. Description will be made in the present embodiment regarding an arrangement in which the digital signal processing unit 116 performs all the steps of the calculation for identifying the base type.

The signal generating circuit 118 generates various kinds of signals to be supplied to the device under test 20. Examples of such signals include: a signal for controlling the electrophoresis electrodes; a signal for controlling the heater; a signal for biasing the electrode pair; and the like. Furthermore, the digital signal processing unit 116 controls the measurement apparatus 1. For example, the digital signal processing unit 116 is provided with a function for controlling the signal generating circuit 118.

The above constitutes a function block diagram of the measurement apparatus 1. Next, description will be made regarding a specific configuration of the measurement apparatus 1. The present inventors have come to recognize the fact that the measurement precision is greatly affected by what kinds of circuit components are included, and by what kind of layout is employed, in the measurement apparatus 1 shown in FIG. 2. Description will be made below regarding a configuration which allows the effects of noise to be reduced, thereby providing high-precision current measurement.

Figure 3:
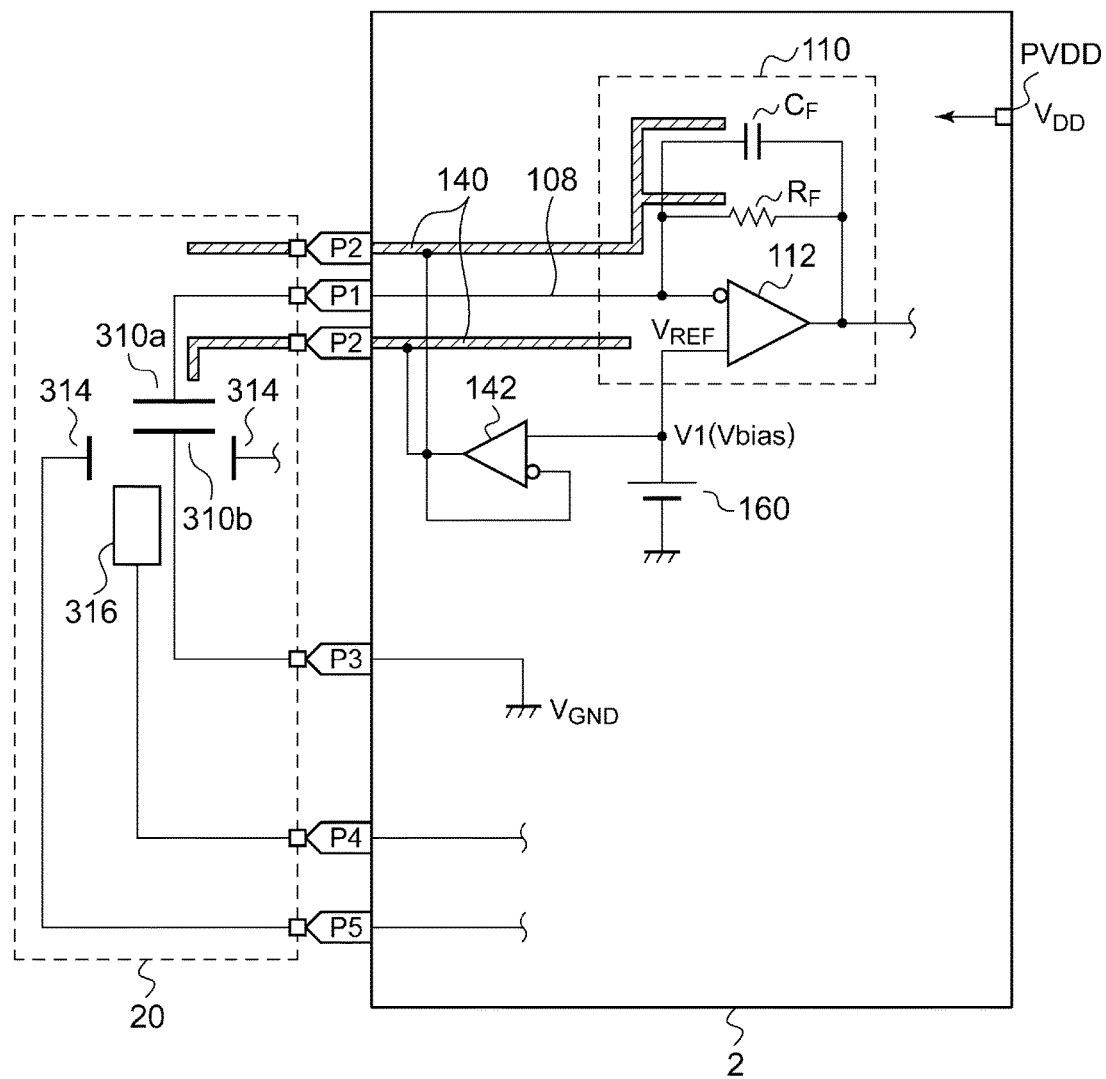
FIG. 3 is a circuit diagram showing an active probe module according to a first example configuration.

First, description will be made regarding a basic configuration. FIG. 3 is a circuit diagram showing the probe module 2 according to a first example. In the present embodiment, the transimpedance amplifier 110 is mounted on the probe module 2. Furthermore, the probe module 2 includes a guard amplifier 142 and a first voltage source 160 as its built-in components. In addition to such circuit components, the probe module 2 may mount other circuit components, which will not be described for ease of understanding and simplification of description.

The transimpedance amplifier 110 includes an inverting amplifier 112, a feedback resistor $R_F$, and a feedback capacitor $C_F$. The feedback resistor $R_F$ and the feedback capacitor $C_F$ are arranged in parallel between the inverting input terminal and the output terminal of the inverting amplifier 112. The transimpedance amplifier 110 is arranged in the vicinity of the pins P1 and P2 to the greatest extent possible. Accordingly, the signal line 108 is designed to have as short a length as possible.

By providing the probe module 2 with the transimpedance amplifier 110 as a built-in component, such an arrangement is capable of converting the current signal $I_{DUT}$ into the voltage signal $V_{OUT}$ in the vicinity of the device under test 20 that generates the current signal $I_{DUT}$. Thus, such an arrangement reduces the noise effects of a digital circuit (not shown) on the transimpedance amplifier 110, thereby providing high-precision measurement. Furthermore, by arranging the transimpedance amplifier 110 such that it is directly in contact with the device under test 20, such an arrangement allows the input capacitance to be reduced. Thus, such an arrangement provides current measurement over a wide bandwidth.

Guard metal members 140 are formed within the probe module 2 such that they are arranged in the vicinity of the signal line 108. The guard metal members 140 may be arranged such that they cover the signal line 108. Preferably, the guard metal members 140 are arranged such that they extend to a position in the vicinity of the input side of the feedback capacitor $C_F$ and a position in the vicinity of the input side of the feedback resistor $R_F$. The guard amplifier 142 is included in the probe module 2 as its built-in component. The guard amplifier 142 applies a virtual ground voltage $V_{REF}$ of the transimpedance amplifier 110 to the guard metal members 140.

Such a configuration allows the guard metal members 140 to block noise mixing in the signal line 108, thereby further reducing noise. Furthermore, by adjusting the electric potential at the guard metal members 140 by means of the guard amplifier 142, such an arrangement is capable of controlling the electric potentials at the guard metal members 140 and the electric potential of the signal line 108 so as to be the same electric potential. Thus, such an arrangement is capable of reducing the effects of a parasitic capacitance that can occur between the guard metal member 140 and the signal line 108, thereby allowing current measurement over a wide bandwidth.

The first voltage source 160 is built into the probe module 2. The first voltage source 160 generates a first voltage V1. The first voltage V1 is supplied to the non-inverting input terminal of the inverting amplifier 112 of the transimpedance amplifier 110 so as to determine the virtual ground voltage $V_{REF}$. The ground voltage $V_{GND}$ (=0 V) is supplied to a second electrode 310b from the probe module 2.

By providing the probe module 2 with the first voltage source 160 as its built-in component, and by generating the first voltage V1 that determines the virtual ground voltage $V_{REF}$ in the vicinity of the transimpedance amplifier 110, such an arrangement is capable of preventing noise from being superimposed on the virtual ground voltage $V_{REF}$. This reduces the noise component of the current signal $I_{DUT}$ or otherwise the noise component of the voltage signal $V_{OUT}$.

In a stable state of the transimpedance amplifier 110, the electric potentials at the inverting input terminal and the non-inverting input terminal of the inverting amplifier 112 are both stabilized to the virtual ground voltage $V_{REF}$. The virtual ground voltage $V_{REF}$ is supplied to a first electrode 310a via the signal line 108. Accordingly, the virtual ground voltage $V_{REF}$ (first voltage V1) is supplied as a bias voltage $V_{BIAS}$ between the first electrode 310a and the second electrode 310b. From this viewpoint, it can be understood that the first voltage V1 determines the bias voltage $V_{BIAS}$ applied between the first electrode 310a and the second electrode 310b.

The probe module 2 is provided with a power supply terminal PVDD for receiving a DC power supply voltage $V_{DD}$. Accordingly, the built-in components of the probe module 2 include no switching power supply generating switching noise. Each active device built into the probe module 2 operates receiving the power supply voltage $V_{DD}$.

There is no need to provide such a switching power supply that functions as a noise source as a built-in component of the probe module 2. Thus, such an arrangement is capable of preventing switching noise from mixing in the input of the transimpedance amplifier 110 or other circuit nodes.

The above is the first example configuration of the probe module 2.

Figure 4:
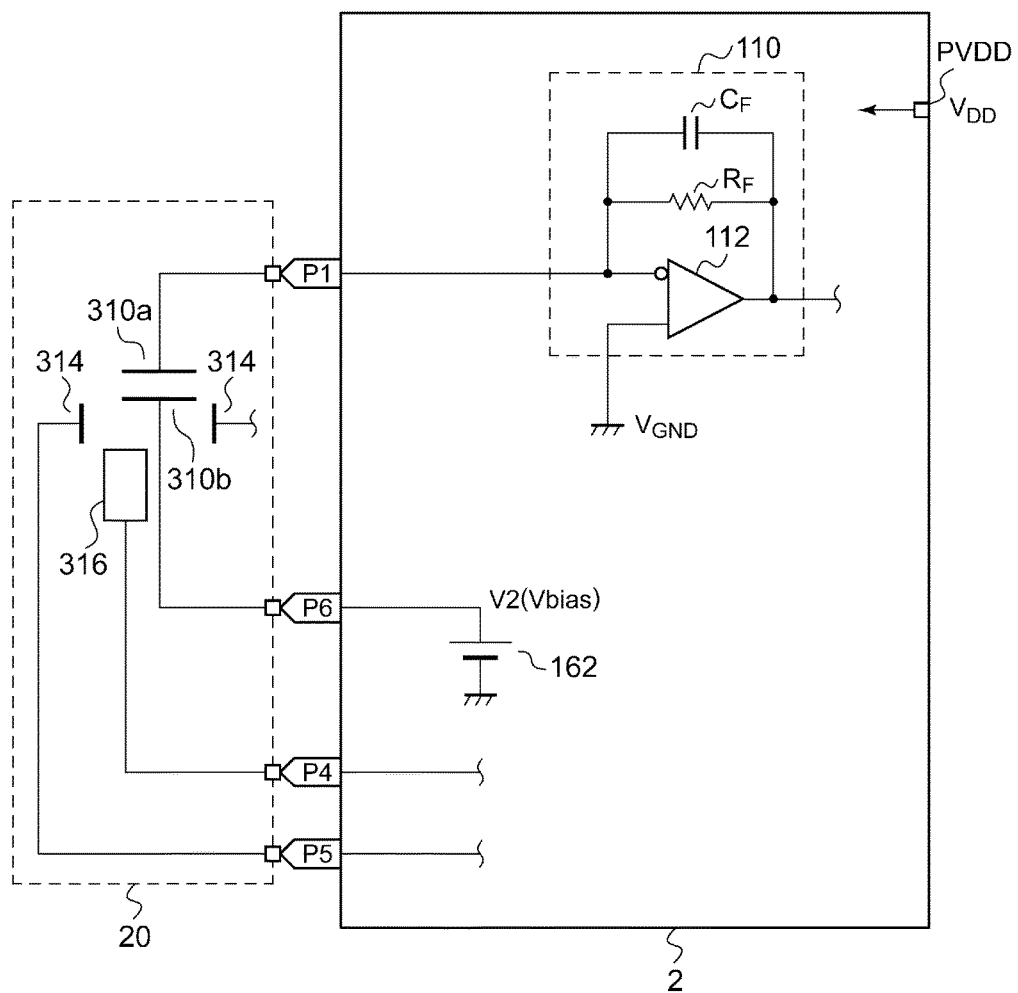
FIG. 4 is a circuit diagram showing an active probe module according to a second example configuration.

FIG. 4 is a circuit diagram showing the probe module 2 according to a second example configuration. As with the first example configuration, the transimpedance amplifier 110 is built into the probe module 2. Thus, such an arrangement is capable of reducing the effect of noise received from a digital circuit (not shown) on the transimpedance amplifier 110, thereby providing high-precision measurement. Furthermore, by arranging the transimpedance amplifier 110 such that it is directly in contact with the device under test 20, such an arrangement allows the input capacitance to be reduced, thereby providing wide-bandwidth current measurement.

A second voltage source 162 is built into the probe module 2. The second voltage source 162 generates a second voltage V2 to be supplied to the device under test 20.

With such a configuration example, the non-inverting input terminal of the inverting amplifier 112 included in the transimpedance amplifier 110 is grounded. Accordingly, the virtual ground voltage is set to the ground voltage $V_{GND}$. The second voltage V2 generated by the second voltage source 162 is supplied to the second electrode 310b. With the transimpedance amplifier 110 in a stable state, the electric potentials at the inverting input terminal and the non-inverting input terminal of the inverting amplifier 112 are both stabilized to the virtual ground voltage $V_{GND}$. The virtual ground voltage $V_{GND}$ is supplied to the first electrode 310a via the signal line 108. When the second voltage V2 is supplied to the second electrode 310b, the second voltage V2 is supplied as the bias voltage $V_{BIAS}$ between the first electrode 310a and the second electrode 310b. From this viewpoint, it can be understood that the second voltage V2 determines the bias voltage $V_{BIAS}$ applied between the first electrode 310a and the second electrode 310b.

With such an arrangement, the second voltage V2, which is to be supplied to the device under test 20, is generated in the vicinity of the device under test 20. Thus, such an arrangement is capable of preventing noise from being superimposed on the second voltage V2. This reduces the noise component of the current signal $I_{DUT}$ or the noise component of the voltage signal $V_{OUT}$.

As with an arrangement shown in FIG. 3, the probe module 2 is provided with the power supply terminal PVDD for receiving the DC power supply voltage $V_{DD}$. Each active device built into the probe module 2 operates receiving the power supply voltage $V_{DD}$. Thus, a built-in switching power supply can be eliminated from the probe module 2, thereby reducing noise effects.

The above is the second example configuration of the probe module 2.

Next, detailed description will be made regarding a specific overall configuration of the measurement apparatus 1.

Figure 5:
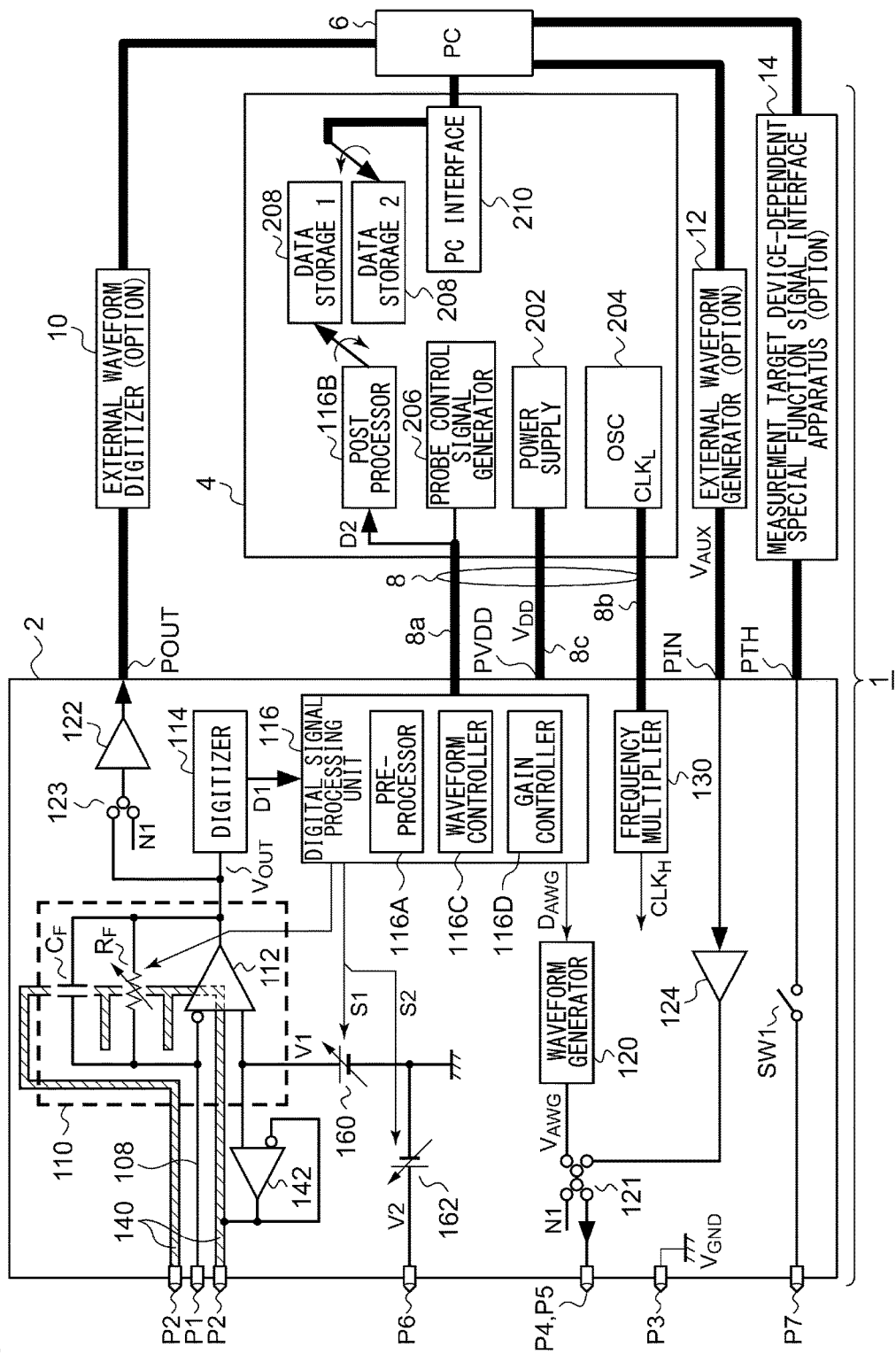
FIG. 5 is a block diagram showing a configuration of a measurement apparatus according to an embodiment.

FIG. 5 is a block diagram showing a configuration of the measurement apparatus 1 according to the embodiment. In FIG. 5, the probe module 2 mainly performs analog signal processing. Furthermore, the probe module 2 performs a part of the digital signal processing as provided by the digital signal processing unit 116 shown in FIG. 2. The probe module 2 and the backend module 4 are connected to each other via multiple cables 8a through 8c. The cable 8a is configured as a digital interface cable. The cable (clock line) 8b is configured as a cable that supplies a clock signal $CLK_L$. The cable (power supply line) 8c is configured as a cable that supplies the DC power supply voltage $V_{DD}$ to the probe module 2 from the backend module 4.

First, description will be made regarding the probe module 2. The probe module 2 shown in FIG. 5 has a hybrid configuration obtained by combining the first configuration example shown in FIG. 3 and the second configuration example shown in FIG. 4. The probe module 2 includes a first voltage source 160, a second voltage source 162, guard metal members 140, and a guard amplifier 142.

The probe module 2 further includes a digitizer 114, digital signal processing units 116A, 116C, and 116D, a waveform generator 120, a first amplifier 122, a second amplifier 124, and a frequency multiplier 130.

The digitizer 114 is built into the probe module 2. The digitizer 114 converts the output $V_{OUT}$ of the transimpedance amplifier 110 into first digital data D1. The first digital signal processing unit (pre-processor) 116A receives the first digital data D1, and executes pre-processing which is a part of a series of signal processing steps for determining the base sequence based on the first digital data D1. The first digital signal processing unit 116A transmits the second digital data (measured signal) D2, which is obtained as a result of the signal processing, to the second digital signal processing unit (post processor) 116B.

That is to say, with such an arrangement shown in FIG. 5, data transmission of the measured signal D2 is performed between the probe module 2 and the backend module 4 via the data I/O cable 8a configured as a digital interface instead of data transmission via an analog interface. By transmitting such a measured signal after it is converted into a digital signal, such an arrangement provides improved resistance to noise in the data transmission process, as compared with an arrangement in which analog data transmission is performed.

For example, the first digital signal processing unit 116A performs pre-processing on the first digital data D1 so as to generate the second digital data D2 having a reduced amount of data, so as to generate the second digital data D2, and transmits the second digital data D2 thus generated to the backend module 4. Examples of such processing for data amount reduction include data compression, data thinning-out, and the like. By compressing the amount of data, such an arrangement allows the transmission rate required for the cable 8a to be reduced, thereby reducing noise emission.

The current signal $I_{DUT}$ is configured as a microscopic signal. Thus, in some cases, in order to identify each base type, a statistical method is employed. The digitizer 114 samples the voltage signal $V_{OUT}$ multiple times (several tens to several hundreds of times) for each base. Accordingly, the first digital signal processing unit 116A receives the first digital data D1 multiple times for each base. Thus, the first digital signal processing unit 116A may reduce the number of bits that represent each first digital data D1, thereby providing a reduced amount of data. Also, the first digital signal processing unit 116A may convert the first digital data D1 into histogram data, thereby providing a reduced amount of data. Also, the first digital signal processing unit 116A may calculate histogram parameters (current average value, current peak value, standard deviation, variance, etc.), and may transmit such parameters thus generated as the second digital data D2.

Data transmission via the cable 8a may be performed in a time slot in which the current measurement is not performed by the transimpedance amplifier 110. Such an arrangement is capable of eliminating the effects of noise that can occur in the data transmission.

A second digital signal processing unit 116B is configured as a part of the digital signal processing unit 116 shown in FIG. 2. The second digital signal processing unit 116B is built into the backend module 4. The second digital signal processing unit 116B receives the second digital data D2 from the first digital signal processing unit 116A, and executes post-processing which is a part of a series of signal processing steps for determining the base sequence. The second digital signal processing unit 116B sequentially writes each base type of the base sequence to a data storage 208 described later.

The first voltage source 160 is configured as a variable voltage source. The first voltage source 160 generates the first voltage V1 having a voltage level that corresponds to a first control signal S1 generated by the first digital signal processing unit 116A (digital signal processing unit 116).

With such an arrangement, the voltage level of the first voltage V1 can be adjusted according to the measurement result (i.e., the first digital data D1) obtained by the digital signal processing unit 116. That is to say, such an arrangement is capable of applying a suitable voltage to the device under test 20 according to the state of the device under test 20.

For example, as a conceivable problem, a signal level of the current signal $I_{DUT}$ can degrade due to abrasion or contamination of the electrode pair 310. In this case, by controlling the first voltage V1 so as to raise the bias voltage $V_{BIAS}$, such an arrangement allows the current signal $I_{DUT}$ to have a large signal level, thereby providing an improved S/N ratio.

Also, the first digital signal processing unit 116A may feedback control the first voltage V1 according to the digital data D1. In this case, this feedback control operation is performed by the probe module 2 alone without involving the backend module 4, thereby providing a high-speed control operation. In addition, the data to be used for the feedback control operation is not transmitted via the cable 8, thereby allowing the noise emission to be reduced.

The second voltage source 162 is configured as a variable voltage source. The second voltage source 162 generates the second voltage V2 having a voltage level that corresponds to a second control signal S2 generated by the first digital signal processing unit 116A (digital signal processing unit 116).

With such an arrangement, the voltage level of the second voltage V2 can be adjusted according to the measurement result (i.e., the first digital data D1) obtained by the digital signal processing unit 116. That is to say, such an arrangement is capable of applying a suitable voltage to the device under test 20 according to the state of the device under test 20.

For example, as a conceivable problem, a signal level of the current signal $I_{DUT}$ can degrade due to abrasion or contamination that occurs in the electrode pair 310. In this case, by controlling the second voltage V2 so as to raise the bias voltage $V_{BIAS}$, such an arrangement is capable of allowing the current signal $I_{DUT}$ to have a large signal level, thereby providing an improved S/N ratio.

Also, the first digital signal processing unit 116A may feedback control the second voltage V2 according to the digital data D1. In a case in which the second voltage V2 is feedback controlled, this feedback control operation is performed by the probe module 2 alone without involving the backend module 4, thereby providing a high-speed control operation. In addition, the data to be used for the feedback control operation is not transmitted via the cable 8, thereby allowing the noise emission to be reduced.

The waveform generator 120 receives digital waveform data $D_{AWG}$, and generates an analog voltage $V_{AWG}$ that corresponds to the digital waveform data $D_{AWG}$. The analog voltage $V_{AWG}$ thus generated is supplied via a pin P4, and is used to perform a heater control operation. Alternatively, the analog voltage $V_{AWG}$ is supplied to the electrophoresis electrodes 314 via a pin P5. Also, multiple waveform generators 120 may be provided so as to generate multiple analog voltages $V_{AWG}$. The waveform generator 120 may be configured as a so-called arbitrary waveform generator. Also, the waveform generator 120 may be configured as a function generator, a D/A converter, or otherwise as another kind of voltage source or signal generator.

A selector 121 may be provided on the output side of the waveform generator 120. The input of the selector 121 may be connected to the output of the waveform generator 120 and the output of a second amplifier 124 described later. Also, the output side of the selector 121 may be connected to the pin P4 or P5, or otherwise to a predetermined node (e.g., input N1 of the selector 123 described later) formed within the probe module 2.

The digital signal processing unit 116 built into the probe module 2 includes a third digital signal processing unit 116C. The third digital signal processing unit 116C generates the digital waveform data $D_{AWG}$ to be used to control the waveform of the analog voltage $V_{AWG}$ generated by the waveform generator 120.

By mounting both the third digital signal processing unit 116C and the waveform generator 120 on the probe module 2, such an arrangement allows the probe module 2 to perform, as its internal operation, a high-speed control operation for controlling the voltage level, the amplitude, and the waveform of the analog voltage $V_{AWG}$.

For example, in a case in which the analog voltage $V_{AWG}$ is supplied to the electrophoresis electrodes 314, the analog voltage $V_{AWG}$ corresponds to a signal for controlling the position of a DNA molecule. The third digital signal processing unit 116C may estimate the position and the velocity of each base based on the first digital data D1, and may adjust the analog voltage $V_{AWG}$ according to the estimation result thus obtained. Also, the third digital signal processing unit 116C may control the analog voltage $V_{AWG}$ using an open loop control method.

In a case in which the analog voltage $V_{AWG}$ is used to control the heater 316, the analog voltage $V_{AWG}$ corresponds to a signal for controlling the temperature of the device under test 20. The third digital signal processing unit 116C may estimate a change in temperature based on the first digital data D1, and may adjust the analog voltage $V_{AWG}$ according to the estimation result thus obtained. Also, the third digital signal processing unit 116C may control the analog voltage $V_{AWG}$ using an open loop control method.

The probe module 2 is further provided with an analog output terminal POUT. The first amplifier 122 is built into the probe module 2. The first amplifier 122 outputs, to an external circuit via the analog output terminal POUT, a signal received from a predetermined internal node included within the probe module 2. Also, a selector 123 may be provided as an input stage of the first amplifier 122, so as to allow multiple nodes to be selected.

In FIG. 5, the selector 123 is capable of selecting one from among the output $V_{OUT}$ of the transimpedance amplifier 110, the analog voltage $V_{AWG}$ which is an output of the waveform generator 120, and the output of a second amplifier 124 described later.

When the selector 123 selects the output of the transimpedance amplifier 110, a high-precision external waveform digitizer 10 is connected to the analog output terminal POUT. Using the external waveform digitizer 10, such an arrangement allows a microscopic current $I_{DUT}$ to be measured. Alternatively, when the selector 123 selects the output of the waveform generator 120, the first voltage source 160, or otherwise the second voltage source 162, such an arrangement allows such an internal circuit (120, 160, or 162) included within the probe module 2 to be calibrated. Also, such an arrangement is capable of providing a diagnostic operation such as a contact check, defective device detection, etc., for the device under test 20.

Furthermore, the probe module 2 is provided with an analog input terminal PIN. The second amplifier 124 is built into the probe module 2. The second amplifier 124 supplies an analog signal $V_{AUX}$ input via the analog input terminal PIN to the device under test 20 and/or to a predetermined internal node included within the probe module 2. By connecting a high-precision external waveform generator 12 such as an arbitrary waveform generator, a function generator, or the like to the analog input terminal PIN, such an arrangement is capable of controlling the heater 316 or the electrophoresis electrodes 314 of the device under test 20, or the bias state of the device under test 20. Alternatively, such an arrangement allows an internal circuit included within the probe module 2 to be calibrated.

Furthermore, the probe module 2 is provided with a probe-through input terminal and a probe-through output terminal (pin) P7. The probe-through input terminal PTH and the probe-through output terminal (pin) P7 are connected with each other directly or otherwise via a switch SW1.

In a case in which a special function signal interface apparatus 14 is connected to the probe-through input terminal PTH, such an arrangement allows a special signal that depends on the device under test to be transmitted and received between the device under test 20 and such an external apparatus 14. Thus, such an arrangement allows the measurement apparatus 1 to measure various kinds of devices under test 20, thereby providing improved compatibility.

The frequency multiplier 130 is built into the probe module 2. The frequency multiplier 130 multiplies the clock signal $CLK_L$ so as to generate a clock signal $CLK_H$ having a higher frequency. The clock signal $CLK_H$ is supplied to the digitizer 114, the digital signal processing unit 116, and the like. The clock signal $CLK_L$, which is an original clock signal, is generated by an oscillator 204 built into the backend module 4.

The current signal $I_{DUT}$ is configured as a microscopic signal. Thus, in some cases, in order to identify each base type, such an arrangement requires a statistical method. In this case, the digitizer 114 is required to sample the output voltage $V_{OUT}$ several tens to several hundreds of times in a very short period of time for each base. Accordingly, the digital signal processing unit 116 is required to perform high-speed calculation processing on the first digital data D1. In this case, in a case in which the probe module 2 includes an oscillator as its built-in component that generates the clock signal $CLK_H$, such an arrangement has the potential to provide degraded detection precision due to noise that occurs in such an oscillator. Alternatively, in a case in which the backend module 4 generates the clock signal $CLK_H$, and supplies the clock signal $CLK_H$ thus generated to the probe module 2 via the clock line 8b, such an arrangement has the potential to have a problem of degraded detection precision due to noise emission.

In the measurement apparatus 1 shown in FIG. 5, the frequency multiplier 130 is built into the probe module 2. Thus, with such an arrangement, the clock signal $CLK_L$ that is transmitted via the clock line 8b can have a low frequency, thereby suppressing the occurrence of noise emission.

The transimpedance amplifier 110 is configured to have a variable gain. For example, the feedback resistor $R_F$ is configured as a variable resistor. The digital signal processing unit 116 includes a gain controller 116D that controls the gain according to the first digital data D1.

Such an arrangement allows the gain to be adjusted based on the measurement result (i.e., first digital data D1) received by the digital signal processing unit 116. Furthermore, in a case in which the gain is feedback controlled, by performing such a feedback control operation in the probe module 2 alone without involving the backend module 4, such an arrangement provides a high-speed control operation. Moreover, with such an arrangement, the data used to perform the feedback control operation is not transmitted via a cable, thereby reducing noise emission.

For example, as a conceivable problem, a signal level of the current signal $I_{DUT}$ can degrade due to abrasion or contamination of the electrode pair 310. In this case, by raising the gain, such an arrangement allows the current signal $I_{DUT}$ to have a large signal level, thereby providing an improved S/N ratio.

The backend module 4 includes a power supply 202 as a built-in component. The power supply 202 generates the power supply voltage $V_{DD}$, and supplies the power supply voltage $V_{DD}$ thus generated to the probe module 2 via the power supply line 8c. It should be noted that the power supply voltage $V_{DD}$ used in the probe module 2 may be supplied from an external power supply to the backend module 4.

The probe control signal generating unit 206 is built into the backend module 4, and controls the overall operation of the probe module 2. The probe control signal generating unit 206 generates a control signal S3, and transmits the control signal S3 thus generated to the digital signal processing unit 116 via the serial interface 8a. The digital signal processing unit 116 operates according to a control operation provided by the probe control signal generating unit 206.

The backend module 4 mounts one or multiple data storages 208. Each data storage 208 may be configured as a hard disk or an SSD (Solid State Drive). The data storage 208 stores the data that represents a base sequence.

The data access timing at which the data storage 208 is accessed may be controlled by the measurement apparatus 1, and more specifically, by the second digital signal processing unit 116B.

The second digital signal processing unit 116B has information with respect to a period for which the digitizer 114 samples a microscopic current. Thus, the second digital signal processing unit 116B may suspend access to the data storage 208 during the measurement of a microscopic current. Thus, such an arrangement is capable of further reducing noise that occurs in the current measurement.

A PC interface 210 is provided in order to allow a computer 6 to be connected to the measurement apparatus 1. The computer 6 controls the backend module 4 and the probe module 2 via the PC interface 210. Furthermore, the computer 6 accesses the data storage 208 so as to read out the base sequence data stored in the data storage 208. The data read-out operation of the computer 6 and the data writing operation of the second digital signal processing unit 116B are performed in an exclusive manner.

Description has been made regarding the present invention with reference to the embodiment. The above-described embodiment has been described for exemplary purposes only, and is by no means intended to be interpreted restrictively. Rather, it can be readily conceived by those skilled in this art that various modifications may be made by making various combinations of the aforementioned components or processes, which are also encompassed in the technical scope of the present invention. Description will be made below regarding such modifications.

[First Modification]

Description has been made in the embodiment regarding an arrangement in which the probe module 2 and the digital signal processing unit 116 of the backend module 4 perform processing up to a base sequence determination. However, the present invention is not restricted to such an arrangement. Also, the second digital signal processing unit 116B may perform processing up to an intermediate step without performing a base sequence determination, and may store intermediate data in the data storage 208. Subsequently, the computer 6 may execute final processing for completing the base sequence determination.

[Second Modification]

Description has been made in the embodiment regarding an arrangement in which the probe module 2 and the backend module 4 each operate according to a control operation of the computer 6. However, the present invention is not restricted to such an arrangement. That is to say, the measurement apparatus 1 may operate as a standalone apparatus without involving the computer 6.

[Third Modification]

The data storage 208 may be detachably connected to the backend module 4. In this case, after the completion of a measurement series by means of the measurement apparatus 1, the user may detach the data storage 208, and may analyze the data using a computer located in a different place.

[Fourth Modification]

The probe module 2 may include a built-in battery. Each active device included within the probe module 2 may operate using the battery as a power supply. Such an arrangement provides the current measurement operation in an environment in which there is no noise that occurs due to a power supply.

[Fifth Modification]

Description has been made in the embodiment regarding a gating nanopore sequencer. Also, the measurement apparatus 1 is applicable to an MCBJ sequencer. In this case, an MCBJ chip is employed instead of a nanopore chip. A conductor member such as a gold wire or the like, a breaking mechanism for breaking the conductor member, and the like are integrated on the MCBJ chip. In this case, the probe module 2 is provided with an amplifier (a part of the signal generating circuit 118) so as to drive the breaking mechanism. Alternatively, the waveform generator 120 may be used as such an amplifier that drives the breaking mechanism.

Furthermore, it can be said that the usage of the measurement apparatus 1 is not restricted to such a DNA sequencer. Also, the measurement apparatus 1 is widely applicable to various kinds of applications that measure a microscopic current.

While the preferred embodiments of the present invention have been described using specific terms, such description is for illustrative purposes only, and it is to be understood that changes and variations may be made without departing from the spirit or scope of the appended claims.

What is claimed is:

1. A measurement apparatus that measures a current signal that flows through a device under test, the measurement apparatus comprising:
    a first pin to be contacted with the device under test;
    a transimpedance amplifier coupled to the first pin and structured to convert the current signal flowing through the device under test through the first pin into a voltage signal proportional to the current signal;
    a digitizer that converts the voltage signal into first digital data; and
    a digital signal processing unit that performs signal processing on the first digital data, and that controls the measurement apparatus,
    a guard metal member formed within the first module such that the guard metal member is located in the vicinity of a signal line via which the current signal is transmitted; and
    a guard amplifier that is built into the first module, and that applies a virtual ground voltage of the transimpedance amplifier to the guard metal member;
    wherein the measurement apparatus has a configuration comprising a first module and a second module which are separated one another, and the first module has the first pin and is located in the vicinity of the device under test during a measurement, and the second module is coupled to the first module via at least one cable, and wherein the transimpedance amplifier is built into the first module.

2. The measurement apparatus according to claim 1, wherein the first module comprises a power supply terminal for receiving a DC power supply voltage.

3. The measurement apparatus according to claim 1, further comprising:
    an analog output terminal provided to the first module; and
    a first amplifier that is built into the first module, and that outputs, to an external circuit via the analog output terminal, a signal received from a predetermined internal node included within the first module.

4. The measurement apparatus according to claim 1, further comprising a data storage built into the second module.

5. The measurement apparatus according to claim 1, further comprising a data storage detachably connected to the second module.

6. The measurement apparatus according to claim 1, further comprising a second pin to be contacted with the device under test and being coupled to the guard metal member,
and wherein the device under test comprises:
a first pad to be contacted with the first pin;
a second pad to be contacted with the second pin;
a path coupled to the first pad, on which the current signal flows; and
a wiring coupled to the second pad, and provided in the vicinity of the path.

7. A measurement apparatus that measures a current signal that flows through a device under test, the measurement apparatus comprising:
a first pin to be contacted with the device under test;
a transimpedance amplifier coupled to the first pin and structured to convert the current signal flowing through the device under test through the first pin into a voltage signal proportional to the current signal;
a digitizer that converts the voltage signal into first digital data; and
a digital signal processing unit that performs signal processing on the first digital data, and that controls the measurement apparatus,
a first voltage source that is built into the first module, and that generates a first voltage that determines the virtual ground voltage of the transimpedance amplifier;
wherein the measurement apparatus has a configuration comprising a first module and a second module which are separated one another, and the first module has the first pin and is located in the vicinity of the device under test during a measurement, and the second module is coupled to the first module via at least one cable,
and wherein the transimpedance amplifier is built into the first module.

8. The measurement apparatus according to claim 7, wherein the first voltage source generates the first voltage having a voltage level that corresponds to a third control signal generated by the digital signal processing unit.

9. A measurement apparatus that measures a current signal that flows through a device under test, the measurement apparatus comprising:
a first pin to be contacted with the device under test;
a transimpedance amplifier coupled to the first pin and structured to convert the current signal flowing through the device under test through the first pin into a voltage signal proportional to the current signal;
a digitizer that converts the voltage signal into first digital data; and
a digital signal processing unit that performs signal processing on the first digital data, and that controls the measurement apparatus;
a second voltage source that is built into the first module, and that generates a second voltage to be supplied to the device under test;
wherein the measurement apparatus has a configuration comprising a first module and a second module which are separated one another, and the first module has the first pin and is located in the vicinity of the device under test during a measurement, and the second module is coupled to the first module via at least one cable,
and wherein the transimpedance amplifier is built into the first module.

10. The measurement apparatus according to claim 9, wherein the second voltage source generates the second voltage having a voltage level that corresponds to a fourth control signal generated by the digital signal processing unit.

11. The measurement apparatus according to claim 9, wherein the device under test comprises a first electrode to be connected to the transimpedance amplifier and a second electrode that faces the first electrode,
wherein a measurement target of the measurement apparatus is a current that flows between the first electrode and the second electrode,
wherein the virtual ground voltage of the transimpedance amplifier is set to the ground voltage,
and wherein the second voltage source supplies the second voltage to the second terminal.

12. A measurement apparatus that measures a current signal that flows through a device under test, the measurement apparatus comprising:
a first pin to be contacted with the device under test;
a transimpedance amplifier coupled to the first pin and structured to convert the current signal flowing through the device under test through the first pin into a voltage signal proportional to the current signal;
a digitizer that converts the voltage signal into first digital data; and
a digital signal processing unit that performs signal processing on the first digital data, and that controls the measurement apparatus,
wherein the measurement apparatus has a configuration comprising a first module and a second module which are separated one another, and the first module has the first pin and is located in the vicinity of the device under test during a measurement, and the second module is coupled to the first module via at least one cable,
and wherein the transimpedance amplifier is built into the first module,
wherein the digitizer is built into the first module.

13. The measurement apparatus according to claim 12, wherein the digital signal processing unit comprises:
a first digital signal processing unit that is built into the first module, that processes the first digital data so as to generate a second digital data having a reduced amount of data, and that transmits the second digital data thus generated to the second module; and
a second digital signal processing unit that is built into the second module, that receives the second digital data from the first digital signal processing unit, and that executes predetermined signal processing.

14. A measurement apparatus that measures a current signal that flows through a device under test, the measurement apparatus comprising:
a first pin to be contacted with the device under test;
a transimpedance amplifier coupled to the first pin and structured to convert the current signal flowing through the device under test through the first pin into a voltage signal proportional to the current signal;
a digitizer that converts the voltage signal into first digital data; and
a digital signal processing unit that performs signal processing on the first digital data, and that controls the measurement apparatus;
a waveform generator that is built into the first module, that receives digital waveform data, and that generates an analog voltage that corresponds to the digital waveform data thus received,
wherein the measurement apparatus has a configuration comprising a first module and a second module which are separated one another, and the first module has the first pin and is located in the vicinity of the device under test during a measurement, and the second module is coupled to the first module via at least one cable,
wherein the transimpedance amplifier is built into the first module; and
wherein the digital signal processing unit is built into the first module, and includes a third digital signal processing unit that generates the digital waveform data.

15. A measurement apparatus that measures a current signal that flows through a device under test, the measurement apparatus comprising:
a first pin to be contacted with the device under test;
a transimpedance amplifier coupled to the first pin and structured to convert the current signal flowing through the device under test through the first pin into a voltage signal proportional to the current signal;
a digitizer that converts the voltage signal into first digital data; and
a digital signal processing unit that performs signal processing on the first digital data, and that controls the measurement apparatus;
an analog input terminal provided to the first module;
a second amplifier that is built into the first module, and that supplies an analog signal input via the analog input terminal to the device under test as well as or otherwise a predetermined internal node included within the first module;
wherein the measurement apparatus has a configuration comprising a first module and a second module which are separated one another, and the first module has the first pin and is located in the vicinity of the device under test during a measurement, and the second module is coupled to the first module via at least one cable,
wherein the transimpedance amplifier is built into the first module.

16. A measurement apparatus that measures a current signal that flows through a device under test, the measurement apparatus comprising:
a first pin to be contacted with the device under test;
a transimpedance amplifier coupled to the first pin and structured to convert the current signal flowing through the device under test through the first pin into a voltage signal proportional to the current signal;
a digitizer that converts the voltage signal into first digital data; and
a digital signal processing unit that performs signal processing on the first digital data, and that controls the measurement apparatus;
an oscillator that is built into the second module, and that generates a clock signal having a predetermined frequency; and
a frequency multiplier that is built into the first module, and that multiplies the clock signal;
wherein the measurement apparatus has a configuration comprising a first module and a second module which are separated one another, and the first module has the first pin and is located in the vicinity of the device under test during a measurement, and the second module is coupled to the first module via at least one cable,
wherein the transimpedance amplifier is built into the first module.

17. A measurement apparatus that measures a current signal that flows through a device under test, the measurement apparatus comprising:
a first pin to be contacted with the device under test;
a transimpedance amplifier coupled to the first pin and structured to convert the current signal flowing through the device under test through the first pin into a voltage signal proportional to the current signal;
a digitizer that converts the voltage signal into first digital data; and
a digital signal processing unit that performs signal processing on the first digital data, and that controls the measurement apparatus,
wherein the measurement apparatus has a configuration comprising a first module and a second module which are separated one another, and the first module has the first pin and is located in the vicinity of the device under test during a measurement, and the second module is coupled to the first module via at least one cable, and wherein the transimpedance amplifier is built into the first module;
wherein the transimpedance amplifier has a variable gain, and wherein the digital signal processing unit is built into the first module, and comprises a gain controller that controls the gain according to the first digital data.

18. A measurement apparatus that measures a current signal that flows through a device under test, the measurement apparatus comprising:
a first pin to be contacted with the device under test;
a transimpedance amplifier coupled to the first pin and structured to convert the current signal flowing through the device under test through the first pin into a voltage signal proportional to the current signal;
a digitizer that converts the voltage signal into first digital data; and
a digital signal processing unit that performs signal processing on the first digital data, and that controls the measurement apparatus,
a probe-through input terminal provided to the first module; and
a probe-through output terminal provided to the first module, and that is connected to the probe-through input terminal;
wherein the measurement apparatus has a configuration comprising a first module and a second module which are separated one another, and the first module has the first pin and is located in the vicinity of the device under test during a measurement, and the second module is coupled to the first module via at least one cable,
and wherein the transimpedance amplifier is built into the first module.

* * * * *